(12) United States Patent  (10) Patent No.: US 7,771,429 B2
Ballard et al.  (45) Date of Patent: Aug. 10, 2010

(54) SURGICAL TOOL FOR HOLDING AND INSERTING FASTENERS

(75) Inventors: Rodney Ray Ballard, Lakeland, TN (US); Jesse Gabriel Moore, Swartz Creek, MI (US); Luis Felipe Aguirre, Brighton, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 777 days.

(21) Appl. No.: 11/467,178

(22) Filed: Aug. 25, 2006

(65) Prior Publication Data

US 2008/0058774 A1    Mar. 6, 2008

(51) Int. Cl.
*A61F 5/00*    (2006.01)
(52) U.S. Cl. ..................... 606/86 R; 606/104
(58) Field of Classification Search ............... 606/53, 606/86 R, 104; 81/57.37, 431, 433; 227/137, 227/120, 117; 124/48
See application file for complete search history.

(56) References Cited

U.S. PATENT DOCUMENTS

| | | | | |
|---|---|---|---|---|
| 333,812 | A | * | 1/1886 | Beal .................... 227/117 |
| 404,166 | A | * | 5/1889 | Burtch et al. .............. 227/70 |
| 452,519 | A | * | 5/1891 | Fernald ................ 227/137 |
| 875,658 | A | * | 12/1907 | Dutton ................. 227/137 |
| 2,222,125 | A | * | 11/1940 | Stehlik ................. 227/116 |
| 2,643,379 | A | | 6/1953 | Matovich |
| 3,009,453 | A | * | 11/1961 | Ayala .................... 124/27 |
| 3,526,257 | A | | 9/1970 | Kirkland |
| 3,604,487 | A | | 9/1971 | Gilbert |
| 3,656,520 | A | * | 4/1972 | Caffa .................... 81/430 |
| 4,124,026 | A | | 11/1978 | Berner et al. |
| 4,763,548 | A | | 8/1988 | Leibinger et al. |
| 5,056,386 | A | | 10/1991 | Chaconas |
| 5,186,084 | A | | 2/1993 | Totsu |
| 5,309,799 | A | | 5/1994 | Jore |
| 5,431,660 | A | | 7/1995 | Burke |
| 5,458,608 | A | | 10/1995 | Wortrich |
| 5,535,729 | A | * | 7/1996 | Griffin et al. ............... 124/66 |
| 5,649,931 | A | | 7/1997 | Bryant et al. |
| 5,690,639 | A | | 11/1997 | Lederer et al. |
| 5,989,289 | A | | 11/1999 | Coates et al. |
| 6,220,122 | B1 | | 4/2001 | Forsell et al. |
| 6,341,542 | B1 | | 1/2002 | Ade et al. |
| 6,415,693 | B1 | | 7/2002 | Simon et al. |
| 6,626,347 | B2 | | 9/2003 | Ng |
| 6,729,522 | B2 | | 5/2004 | Hempfling et al. |
| 6,941,627 | B2 | | 9/2005 | Fritsche et al. |
| 2002/0020255 | A1 | | 2/2002 | Simon et al. |
| 2002/0121539 | A1 | | 9/2002 | Strong et al. |
| 2002/0166421 | A1 | | 11/2002 | Bowerman |
| 2003/0150897 | A1 | | 8/2003 | Ng |
| 2003/0191478 | A1 | | 10/2003 | Kortenbach et al. |
| 2005/0115370 | A1 | | 6/2005 | Totsu |
| 2005/0131408 | A1 | | 6/2005 | Sicvol et al. |
| 2005/0256529 | A1 | | 11/2005 | Yawata et al. |
| 2005/0261691 | A1 | | 11/2005 | Hester et al. |

* cited by examiner

*Primary Examiner*—Thomas C Barrett
*Assistant Examiner*—Michael J Araj

(57) ABSTRACT

Surgical tools and methods for inserting fasteners into a patient. The tools may be loaded to hold multiple fasteners at a single time. The tools may include an elongated shape for insertion into the patient and placement at a predetermined position. A dispensing mechanism within the tools individually releases the fasteners. The tools may further be equipped to completely or partially mount the fasteners within the patient. Methods of using the tools include preloading chambers with multiple fasteners prior to the surgical procedure. The fasteners may then be individually released from the tools during the surgical procedure and carefully positioned within the patient.

17 Claims, 13 Drawing Sheets

SURGICAL TOOL FOR HOLDING AND INSERTING FASTENERS

BACKGROUND

The present application is directed to a surgical tools and methods for holding fasteners and, more particularly, to a tool that holds fasteners and individually delivers the fasteners to a predetermined position within a patient.

Fasteners are inserted into a patient during a variety of surgical procedures. The fasteners are normally inserted into bone or tissue to secure the implant at a predetermined position within the patient. Fasteners may also be inserted within the implant itself. Often times multiple fasteners are needed during a surgical procedure. Further, the surgical procedure may include inserting multiple implants into the patient. At least one fastener may be needed to for each implant.

The fasteners may be small and difficult to manually handle by the surgeon. The size may prevent the surgeon from accurately locating the fastener within proximity to the predetermined position within the patient. The size may also make it difficult for the surgeon to attach the fastener to an insertion tool. Bodily fluid may further complicate the handling by making the fastener more difficult to grasp and manipulate.

An insertion tool should securely handle the fastener during the surgical procedure. During insertion, the fasteners should be secure until placed within the predetermined position within the patient to prevent the fastener from be misplaced within the patient. Exterior to the patient, the tool should prevent inadvertent separation of the fasteners from the tool that may cause the fastener to fall to the operating room floor and require the fastener to be sterilized before being inserted within the patient.

SUMMARY

The present application is directed to surgical tools and methods for holding and inserting fasteners within a patient. The tools may include a holder for maintaining one or more fasteners, and a discharge port positioned adjacent to the holder. In one embodiment, the holder may be indexed to move one of the fasteners into the discharge port. In another embodiment, the discharge port may be indexed relative to the holder. The discharge port is sized to direct the fastener to a specific location within the patient.

One method of use comprises a movable member that is actuated by the surgeon. The actuation causes the holder to rotate relative to the discharge port. The rotation causes the fasteners housed within the holder to move into the discharge port. This tool may allow the surgeon to individually deliver fasteners to predetermined positions within the patient.

BRIEF DESCRIPTIONS OF THE DRAWINGS

DETAILED DESCRIPTION

The present application is directed to surgical tools and methods for inserting fasteners into a patient. The tools may be loaded to hold one or more fasteners at a single time. The tools may include an elongated shape for insertion into the patient and placement at a predetermined position. A dispensing mechanism within the tools individually releases the fasteners. The tools may further be equipped to completely or partially align the fasteners within the patient.

Figure 1:
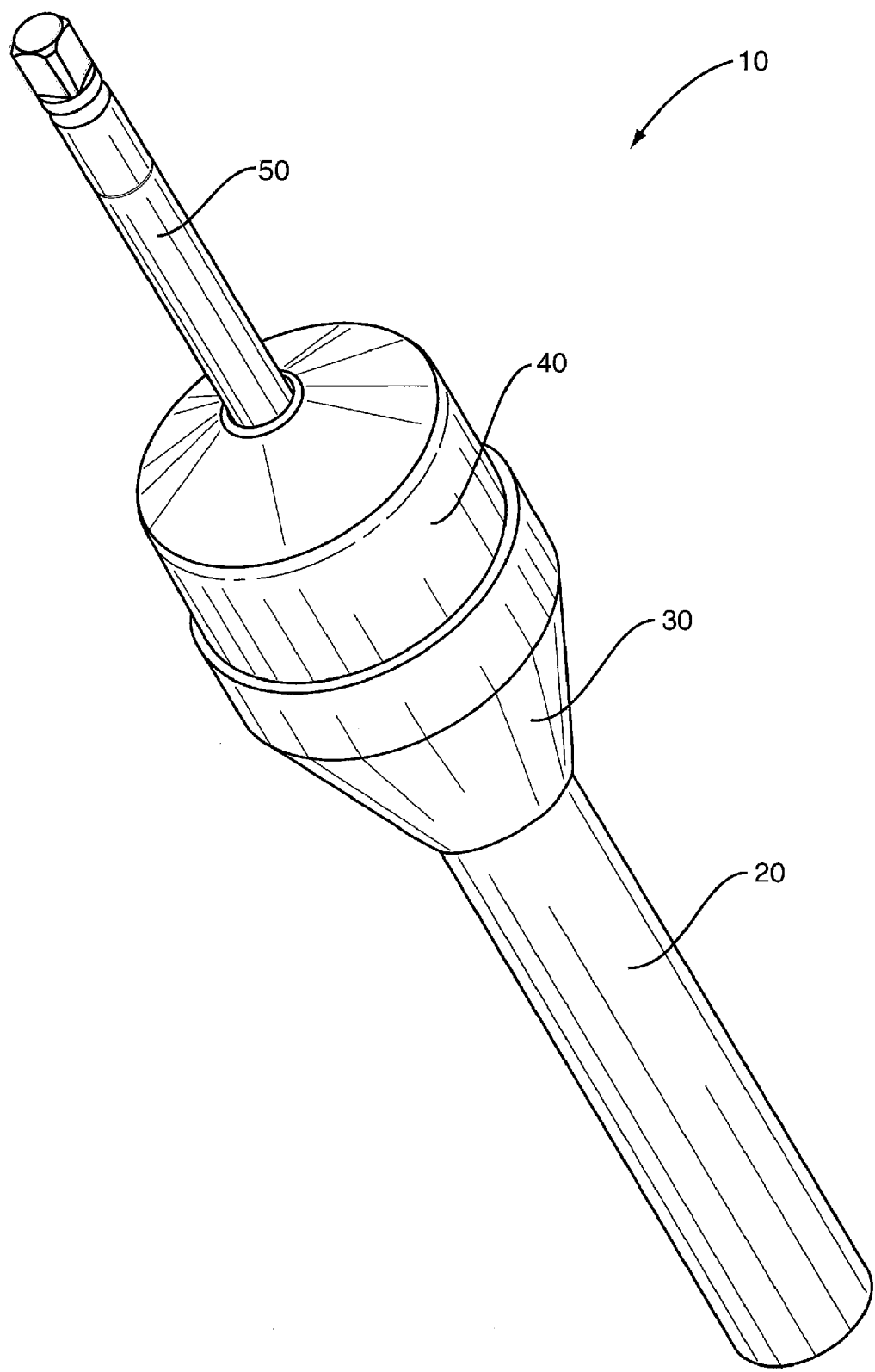
FIG. 1 is a perspective view of a tool for holding one or more fasteners according to one embodiment.
Figure 2:
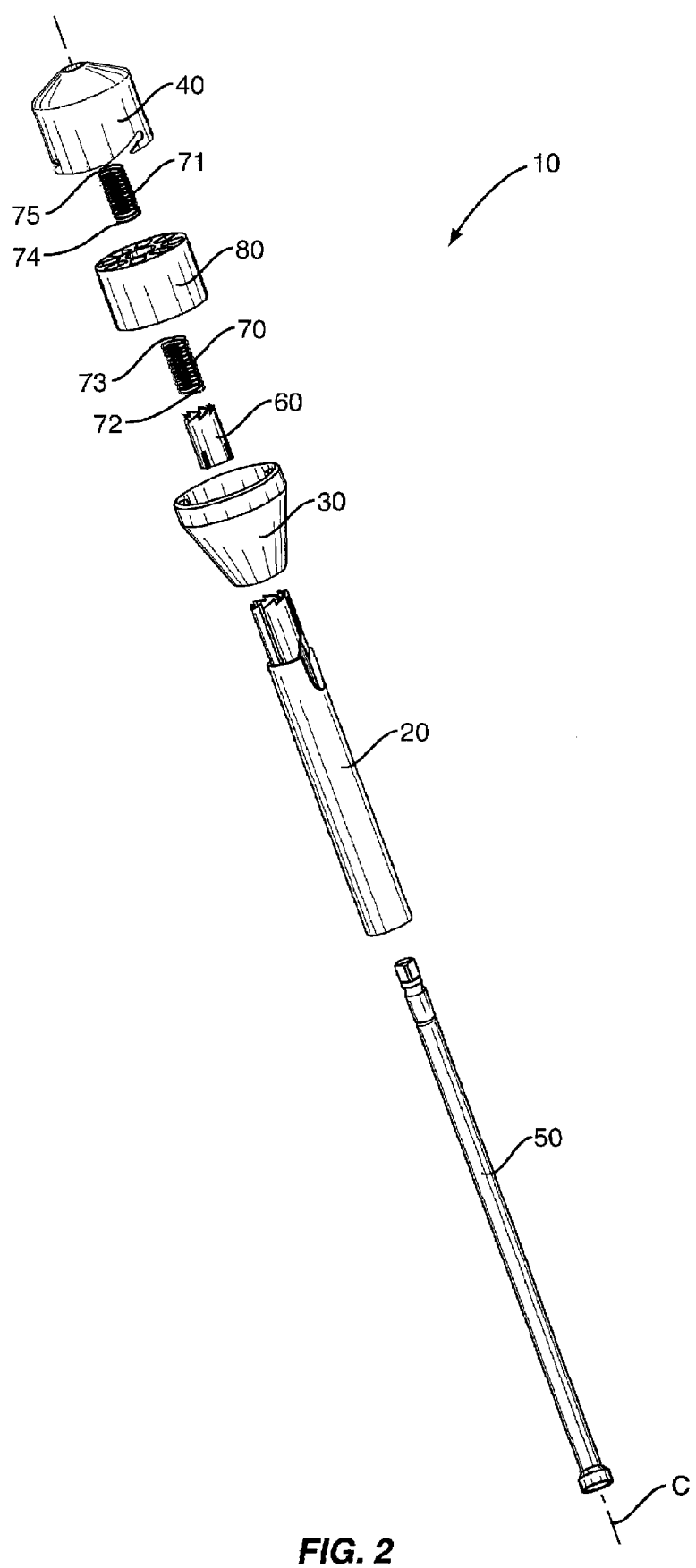
FIG. 2 is an exploded perspective view of a tool according to one embodiment.

FIG. 1 illustrates one embodiment of a tool 10. The size of the tool 10 allows for manual manipulation by the surgeon and for insertion of the entirety or a section into the patient. The tool 10 includes an elongated shell 20, a chute 30, and a shaft 50. A lid 40 is positioned to cover the fasteners that are positioned within a cartridge 80 (FIG. 2). The fasteners are housed within the cartridge 80 and individually dispensed by movement of the shaft 50. The fasteners move from the cartridge 80 through the chute 30 and into shell 20 where they may be accurately positioned within the patient.

FIG. 2 is an exploded view illustrating the elements of one embodiment of a tool 10. Each of the elements is aligned along a centerline C that extends through the tool 10. The cartridge 80 is constructed to house the fasteners and is positioned between the chute 30 and lid 40. The shell 20 extends from the chute 30 on a side opposite from the lid 40. A shaft 50 extends through each of these elements. A rod pin 60 and a pair of springs 70, 71 are positioned for rotating the cartridge 80 during axial movement of the shaft 50. The rotation causes a fastener housed in the cartridge 80 to be dispelled and move through the chute 30 and shell 20. The tool 10 may then be used to accurately place the fastener within the patient.

Figure 3:
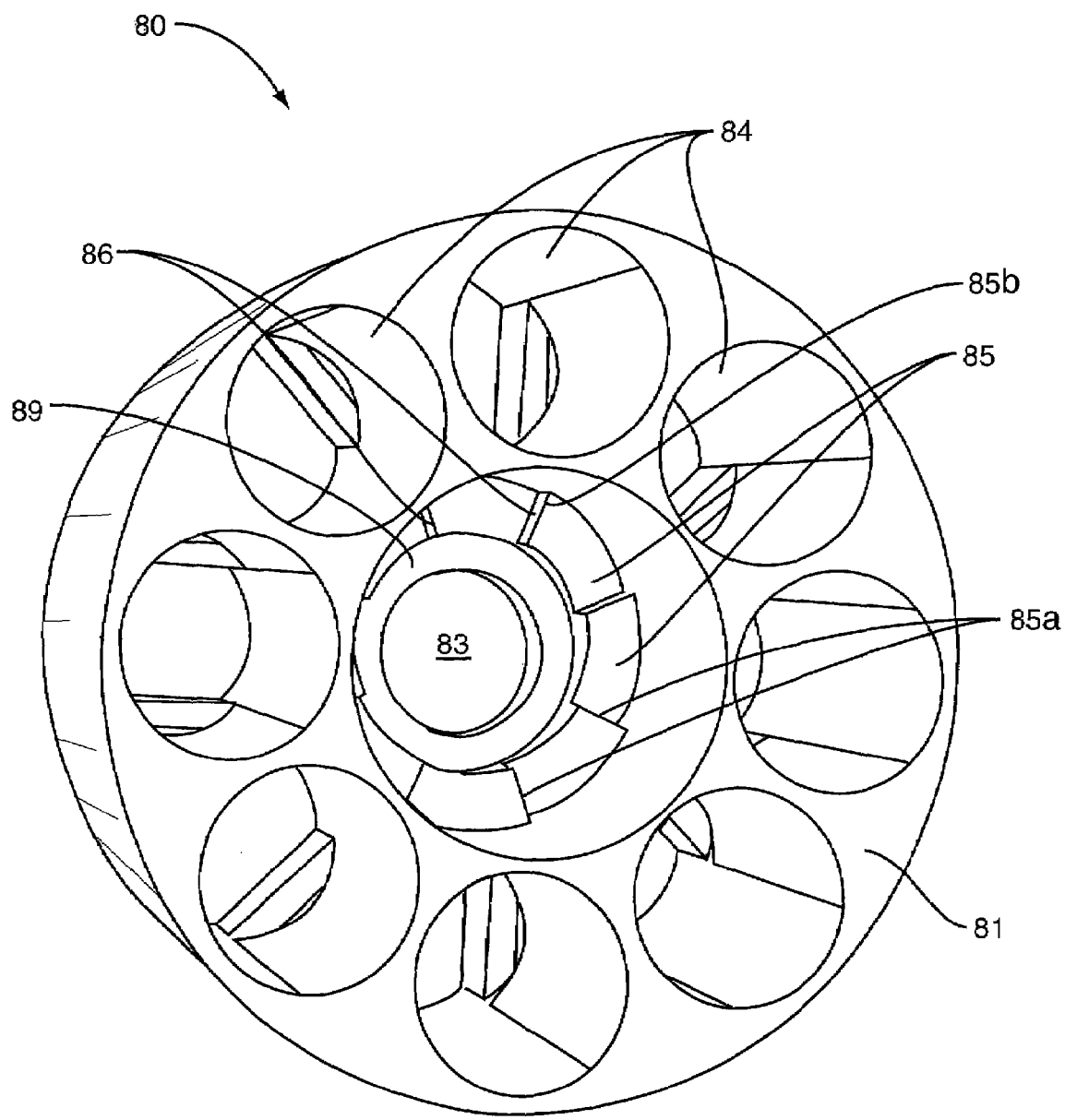
FIG. 3 is a perspective view of a first end of a cartridge according to one embodiment.
Figure 4:
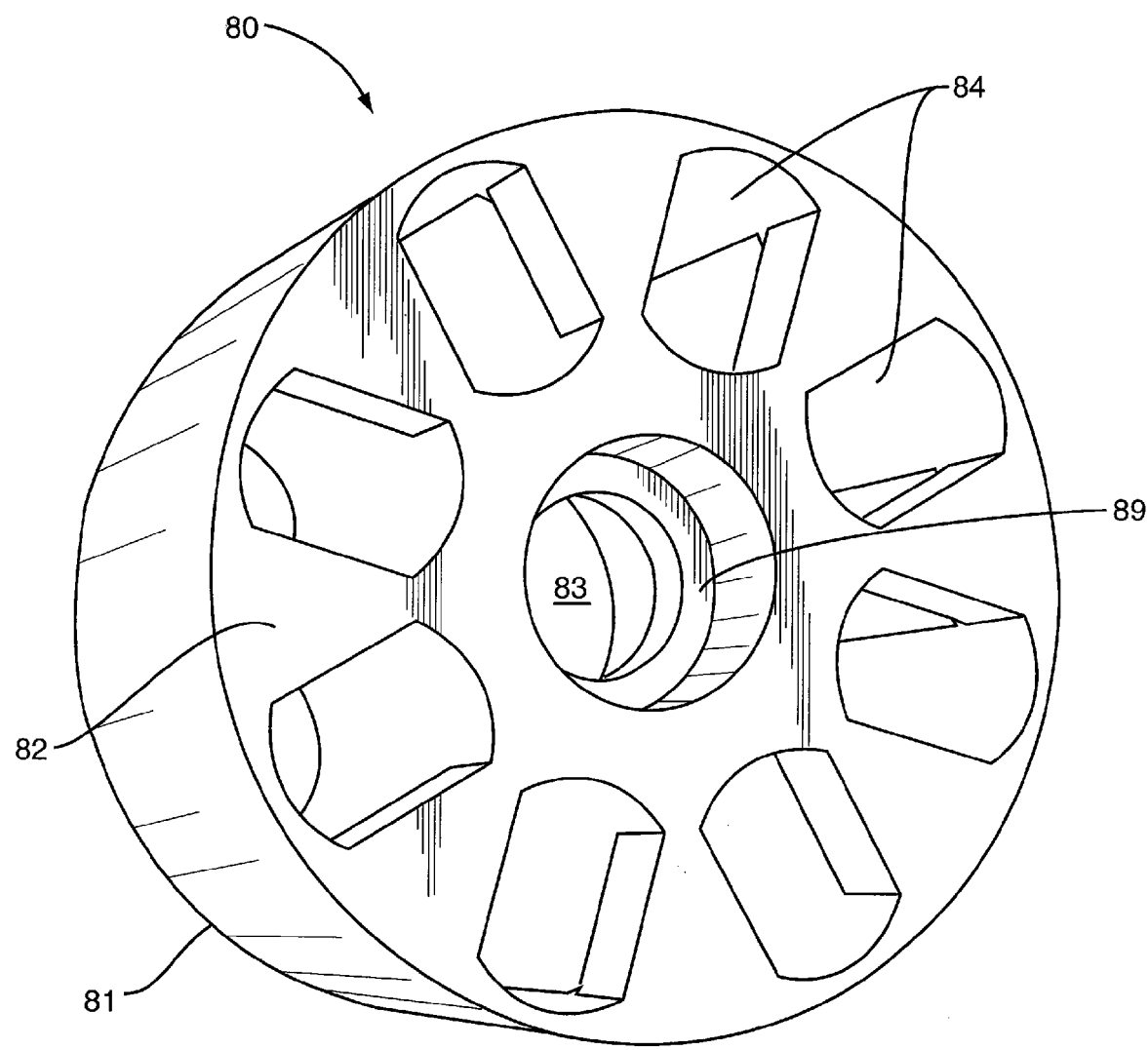
FIG. 4 is a perspective view of a second end of a cartridge according to one embodiment.

FIGS. 3 and 4 illustrate one embodiment of the cartridge 80. Cartridge 80 is substantially cylindrical in shape with a first end 81 that faces downward towards the shell 20, and a second end 82 that faces upward towards the lid 40. An opening 83 extends through the center of the cartridge 80 and is aligned with the centerline C of the tool 10. A plurality of teeth 85 are positioned around the periphery of the aperture 83 and face downward towards the first end 81. Each tooth 85 includes a ramped section with a first end 85a and a raised second end 85b, and a vertical section 86. In one embodiment, each tooth 85 is substantially the same.

A plurality of chambers 84 are radially positioned outward from the central opening 83. Each chamber 84 is sized to receive a fastener. In the embodiment of FIGS. 3 and 4, the cartridge 80 includes eight chambers 84. Other embodiments may feature different numbers of chambers 84 depending upon the size of the cartridge 80 and fasteners. In one embodiment, the chambers 84 include a substantially uniform cross-sectional shape through the cartridge 80. In another embodiment as illustrated in FIGS. 3 and 4, the cross-sectional shape changes. The chambers 84 include a substantially circular cross-sectional shape that extends inward from the first end 81 and a substantially rectangular shape that extends inward from the second end 82. The circular cross-sectional shape is slightly larger than the fasteners and the rectangular cross-sectional shape is slightly smaller than the fasteners. During loading of the fasteners, the tool 10 is inverted with the first end 81 facing vertically upward. The tool 10 is opened and the fasteners may be inserted into the chambers 84 from the first end 81 with gravity causing each to move through the circular section and contact the rectangular section. After loading, the tool 10 is closed with the fasteners being maintained within the chambers 84.

Figure 5:
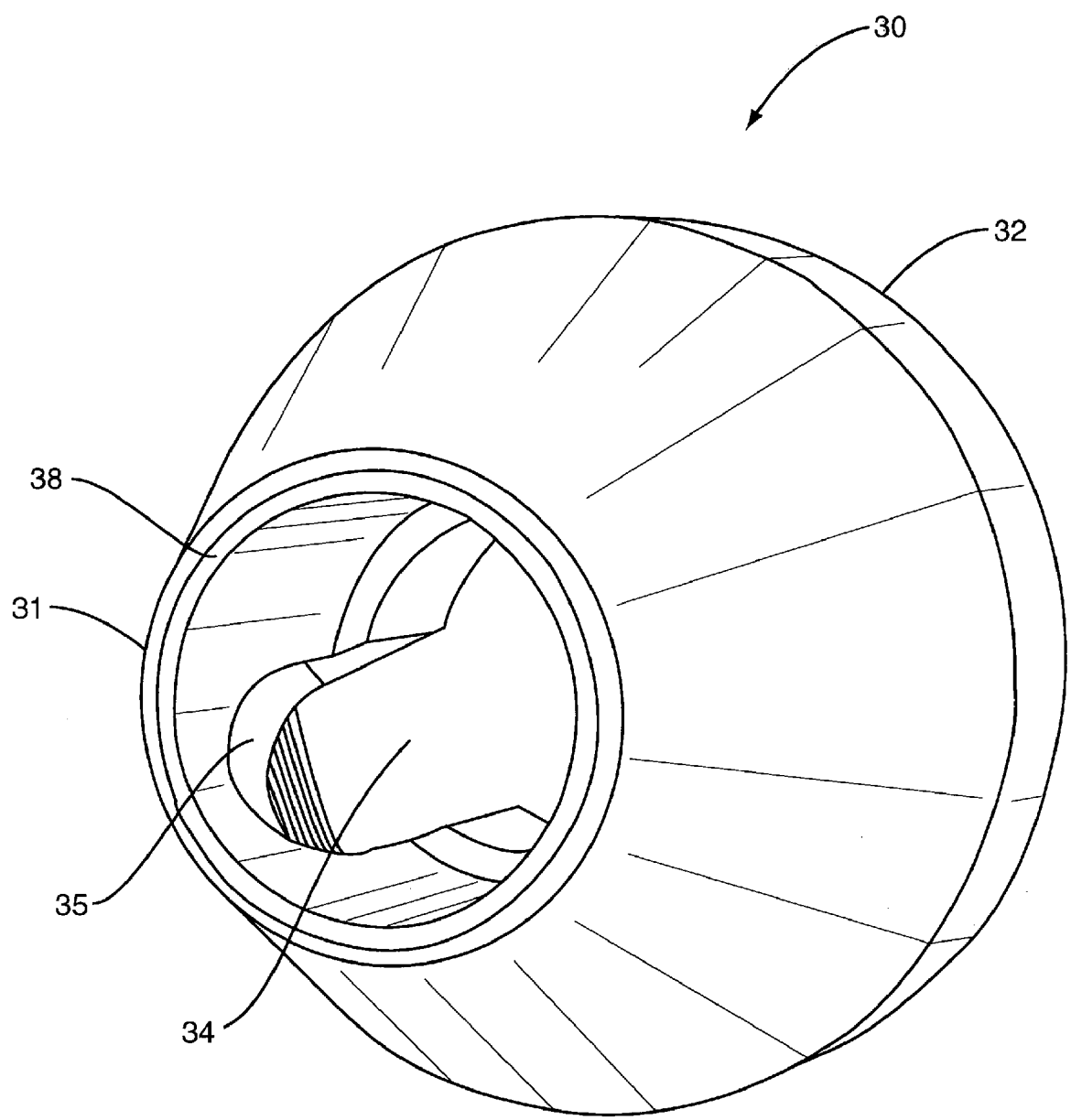
FIG. 5 is a perspective view of a first end of a chute according to one embodiment.
Figure 6:
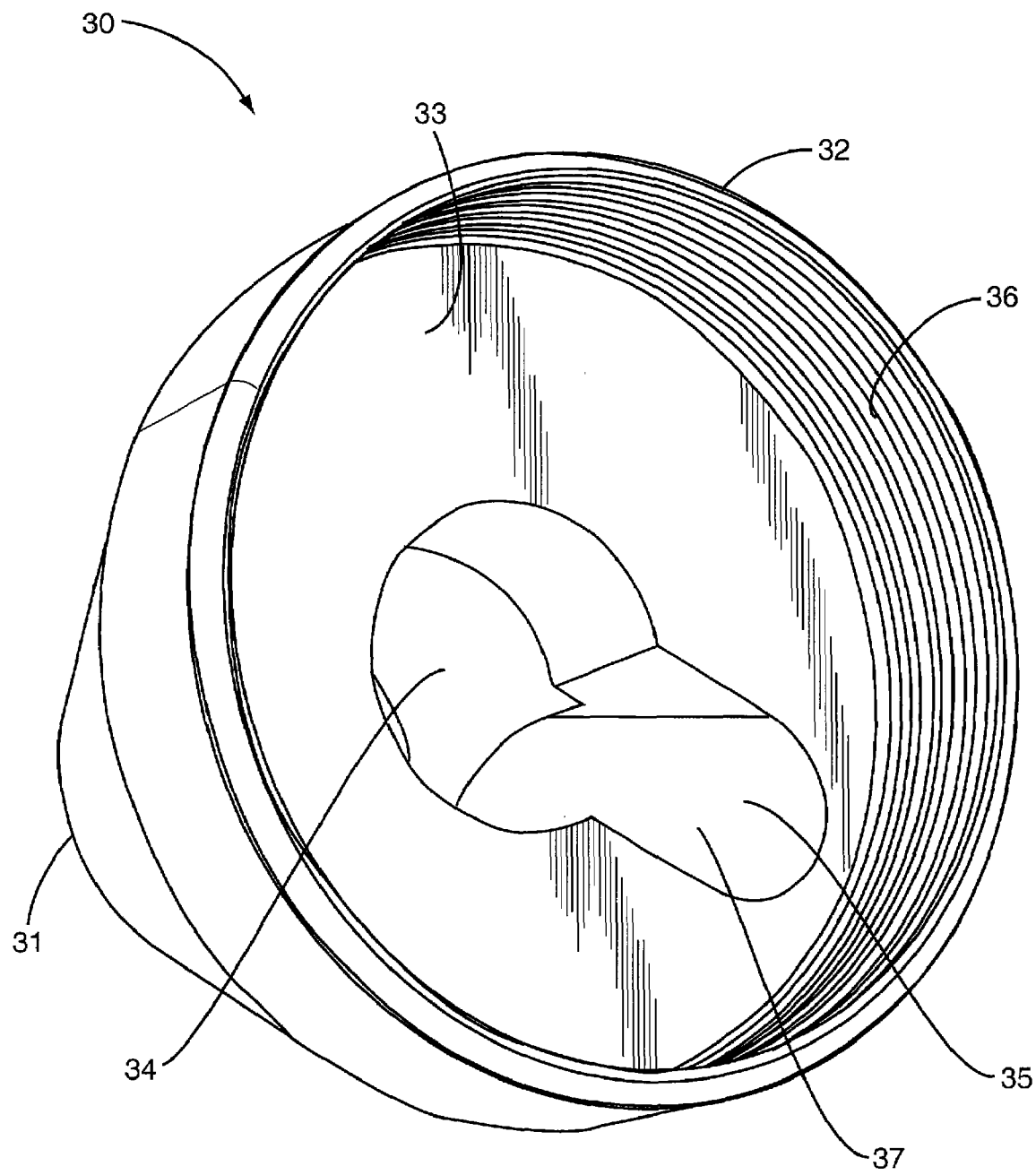
FIG. 6 is a perspective view of a second end of a chute according to one embodiment.

The chute 30 is aligned on the first end 81 of the cartridge 80. The chute 30 receives the fasteners as they are released from the cartridge 80 and directs them into the shell 20. As illustrated in FIGS. 5 and 6, chute 30 includes a substantially conical shape with a narrow first end 31 and an enlarged second end 32. In one embodiment, the second end 32 is large enough to extend around and receive the first end 81 of the cartridge 80. In another embodiment, the second end 32 abuts against the cartridge first end 81. A central opening 34 extends through the chute 30 and is sized to allow the fasteners to pass through. A cut-out section 35 extends radially outward from the central opening 34. Cut-out section 35 includes a larger width towards the second end 32 and narrows towards the first end 31. A bottom surface 37 ramps downward towards the first end 31. The first end 31 further includes a contact surface 33 adjacent to the cut-out section 35. The contact surface 33 supports the fasteners within the chambers 84. The contact surface 33 prevents the fasteners from inadvertently exiting the cartridge 80 until the specific chamber is rotated over the cut-out section 35. Once the specific chamber is positioned over the cut-out section 35, the fastener falls via gravity with the leading edge of the fastener contacting the bottom surface 37. The ramped configuration of the cut-out causes the fasteners to move radially inward towards the centerline C as they move through the chute 30.

Figure 7:
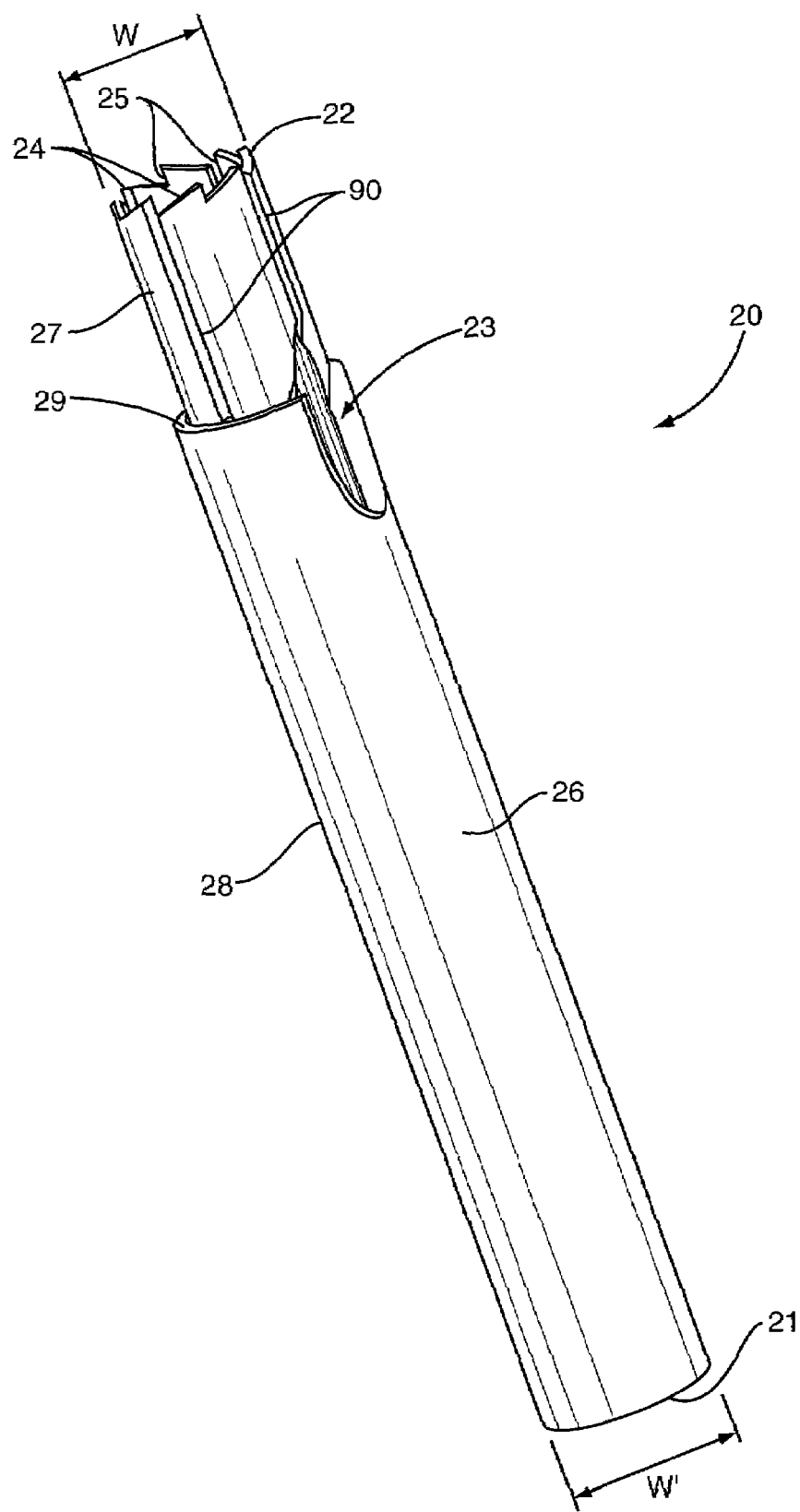
FIG. 7 is a perspective view of a shell according to one embodiment.

The shell 20 is attached to the first end 31 of the chute 30. As illustrated in FIG. 7, the shell 20 is substantially cylindrical with a first end 21 and a second end 22. An opening 23 extends through a sidewall 26 and into a hollow interior. A second section 27 at the second end 22 includes a width W that is less than a width W' of a first section 28. The change in width between the sections 27, 28 forms a shelf 29 positioned between the first and second ends 21, 22. The second end 22 is sized to fit into the opening 34 at the first end 31 of the chute 30. In one embodiment, the extent of insertion of the shell 20 into the chute 30 is established when the shelf 29 abuts against a shelf 38 at the first end 31. The shell 20 is oriented within the chute 30 with the opening 23 aligned with the cut-out 35. During use, the fasteners move through the cut-out 35 and central opening 34 and into the opening 23 to the hollow interior of the shell 20. In one embodiment as illustrated in FIG. 7, the opening 23 straddles the shelf 29 formed between the first and second sections 27, 28.

Teeth 24 are positioned on the second end 22. Each tooth 24 is similar to the cartridge teeth 85 described above and includes a ramped length with a vertical section 25. The shell teeth 24 contact against the cartridge teeth 85 when the tool 10 is in a first orientation as will be explained in detail below. In one embodiment, the teeth 24, 85 include complementary shapes and sizes.

The second end 22 also includes one or more slots 90. The slots 90 extend inward a predetermined distance to receive the rod pin 60. In one embodiment, the slots 90 are substantially straight and parallel with the centerline C.

Figure 8:
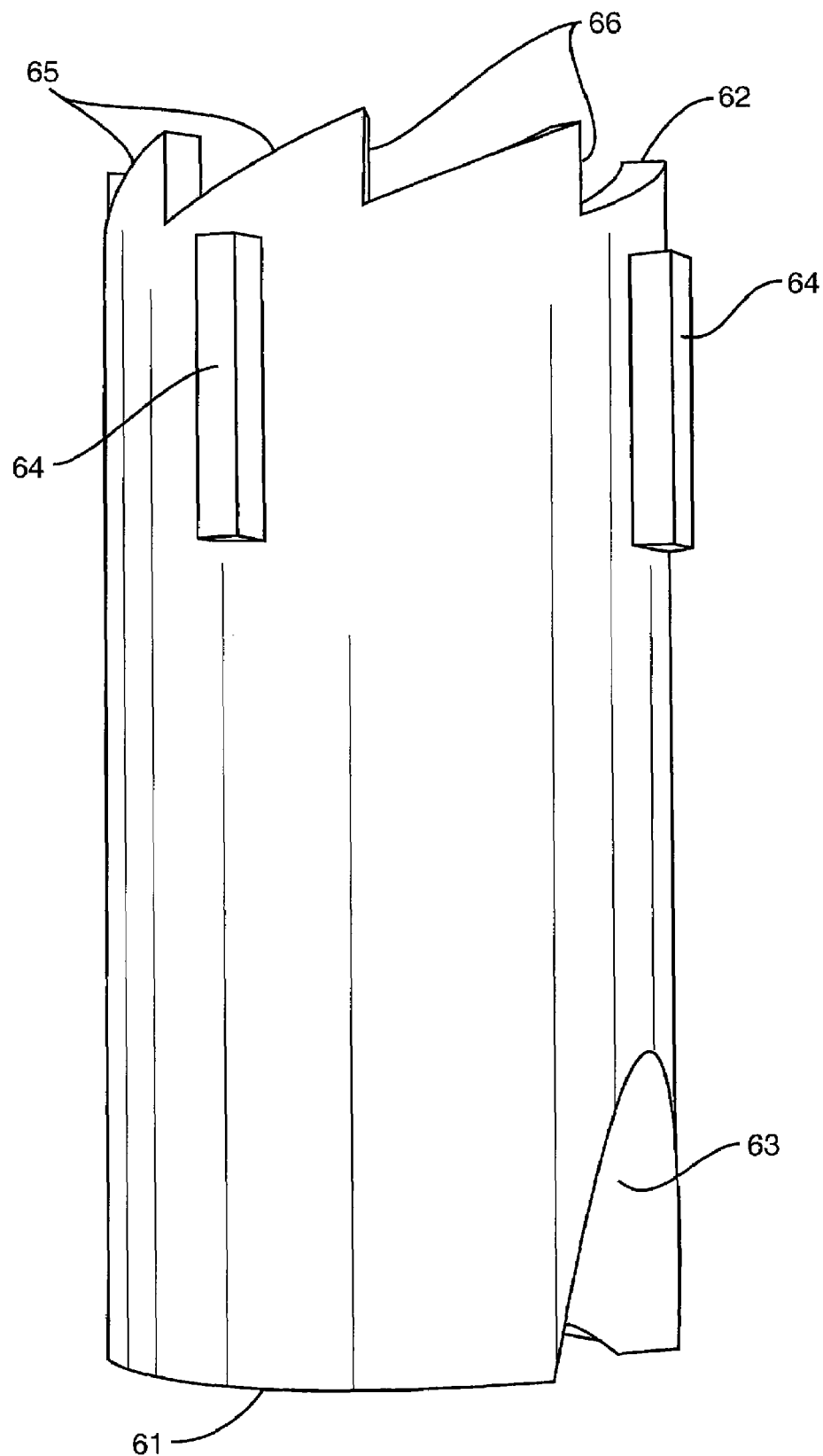
FIG. 8 is a side view of a rod pin according to one embodiment.
Figure 9:
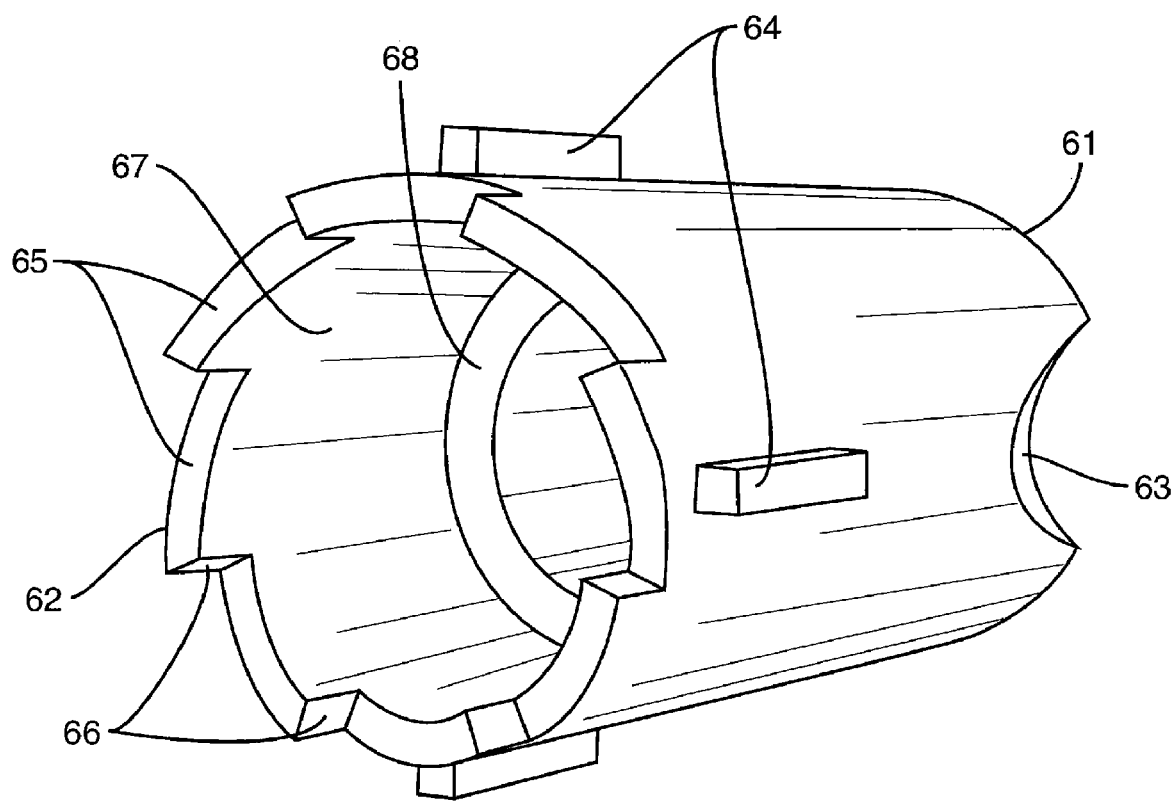
FIG. 9 is a perspective view of a second end of a rod pin according to one embodiment.

Rod pin 60 is positioned within the second end 22 of the shell 20. As illustrated in FIGS. 8 and 9, rod pin 60 is substantially cylindrical with first and second ends 61, 62. The rod pin 60 includes a hollow interior 67 that includes a shelf 68. The diameter of the interior 67 is greater at the second end 62 above the shelf 68, and smaller from the shelf 68 to the first end 61. A cut-out section 63 at the first end 61 leads into a hollow interior 67. The cut-out section 63 aligns with the cut-out section 35 of the chute 30 and the opening 23 of the shell 20 to form a pathway for the fastener.

Teeth 65 extend around the periphery of the second end 62. Each tooth 65 includes a ramped length and a vertical section 66. Teeth 65 may each include substantially the same shape and ramp angle, and may be similar to the teeth 85, 24 discussed above. The teeth 65 contact the cartridge teeth 85 to rotate the cartridge 80 as will be explained in detail below.

Rod pin 60 further includes one or more extensions 64 that extend outward from the sidewalls. The extensions 64 are substantially straight and parallel with the centerline C. Extensions 64 fit within the slots 90 of the shell 20 to prevent relative rotation between the rod pin 60 and the shell 20. The extensions 64 are sized to allow axially sliding within the slots 90 thus allowing for the rod pin 60 to move axially relative to the shell 20. The extensions 64 also rotationally position the rod pin 60 relative to the shell 20. In one embodiment, the relative positions include offsetting the teeth 65, 24. This includes the step 25 of the shell being positioned along the ramped surface of the teeth 65. Likewise, step 66 is positioned along the ramped surface of teeth 24. This offset orientation facilitates rotation of the cartridge 80 as will be explained below.

Figure 10:
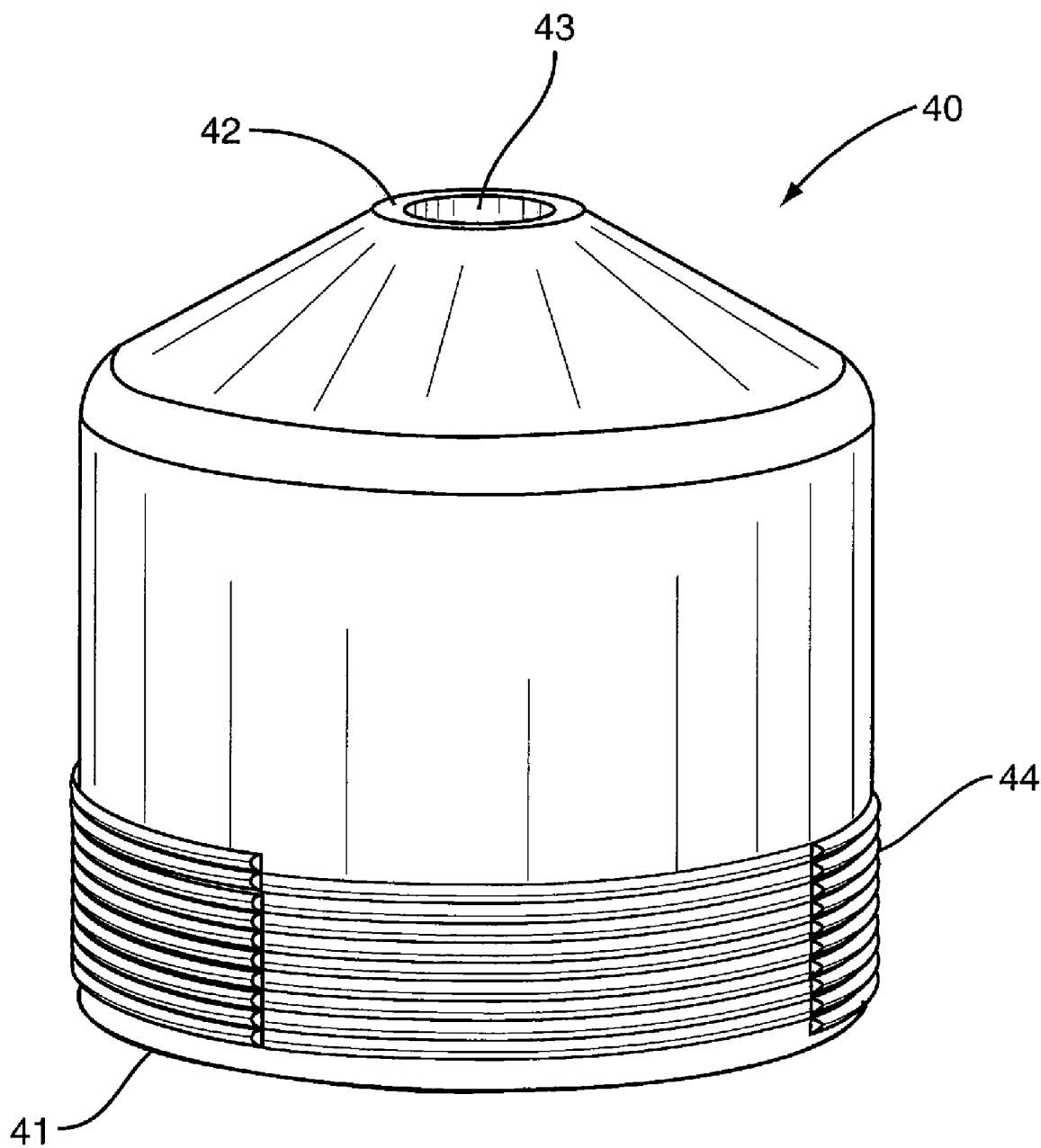
FIG. 10 is a perspective view of a lid according to one embodiment.

The lid 40 extends over the cartridge 80. FIG. 10 illustrates one embodiment of a lid 40 with a first end 41 and a second end 42. The first end 41 is sized to extend around the cartridge 80. Threads 44 may be positioned to mate with threads 36 on the chute 30 thereby forming a contained enclosure in which the cartridge 80 is positioned. An opening 43 extends through the lid 40 to receive the shaft 50. Lid 40 also retains the spring 71 as will be explained below.

Figure 11:
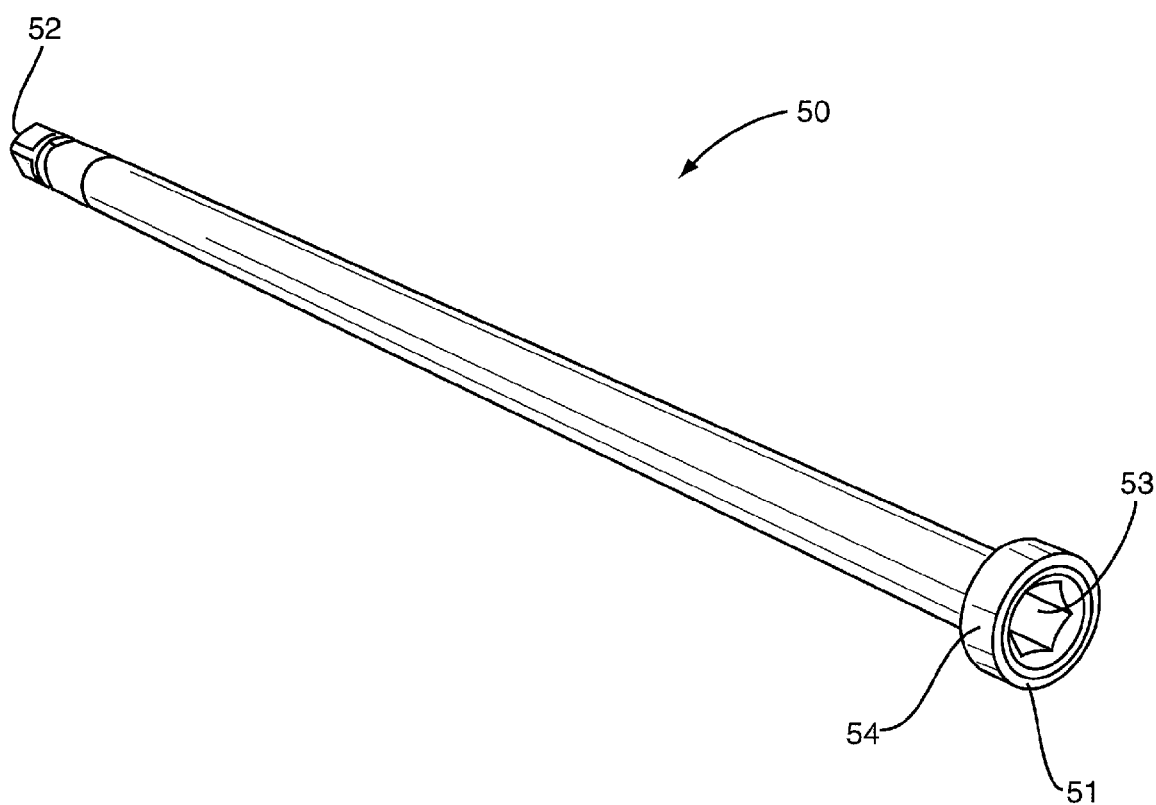
FIG. 11 is a perspective view of a shaft according to one embodiment.

The shaft 50 includes an elongated body with a first end 51 and a second end 52 as illustrated in FIG. 11. The first end 51 may include an enlarged head 54 with a receptacle 53 sized to fit with the fastener. The receptacle 53 may include a variety of different shapes to accommodate different types of fasteners, such as but not limited to Torx, hexagon, flathead, and Phillips. A handle (not illustrated) may be attached to the second end 52 to move the shaft 50 in axial directions. The shaft 50 extends through the center of the tool 10 including the lid opening 43, cartridge opening 83, the opening in the rod pin 60, chute opening 34, and the shell 20. Shaft 50 further extends through springs 70, 71.

Springs 70, 71 bias the tool 10 towards a closed orientation. Each spring 70, 71 may be substantially similar or may be different. In one embodiment, each spring 70, 71 is a coil spring with a center opening sized to receive the shaft 50. Spring 70 includes a first end 72 that contacts the shelf 68 of the rod pin 60 and a second end 73 that contacts the shelf 89 that faces the first end 81 of the cartridge 80. Spring 71 includes a first end 74 that contacts the cartridge shelf 88 that faces the second end 82 and a second end 75 that contacts the lid 40.

The tool 10 is adjustable between a closed orientation and an open orientation. In the open orientation, the cartridge first end 81 is separated from the chute 30 to insert fasteners into the chambers 84. In one embodiment, the tool 10 is inverted with the first end 81 facing vertically upward to receive the fasteners. In the closed orientation, the cartridge first end 81 is adjacent to the chute 30 with the chute contact surface 33 supporting the fasteners within the chambers 84. In one embodiment, the tool 10 assumes the closed orientation when no external forces are acting on the tool 10.

When the tool 10 is in the closed orientation, the shaft 50 may be axially moved to discharge the fasteners. Axial movement of the shaft 50 causes two separate events. First, the movement causes the cartridge 80 to rotate and align one of the chambers 84 over the cut-out 35 of the chute 30. Second, the movement causes the first end 51 of the shaft 50 to move above the contact surface 33 of the chute 30 thereby allowing a fastener to move through the cut-out 35 and opening 34 and into the shell 20.

Prior to movement of the shaft 50, the biasing force of the springs 70, 71 causes the cartridge teeth 85 to contact the shell teeth 24. In one embodiment with this orientation, the second end 62 of the rod pin 60 is below the second end 22 of the shell 20. Movement of the shaft 50 in an axial upward direction causes the enlarged head 54 of the shaft 50 to contact the first end 61 of the rod pin 60. This occurs when the surgeon grasps the shaft 50 in proximity of the second end 52 and pulls upward. Upward movement of the shaft 50 causes the shaft head 54 to move the rod pin 60 upward along the shell 20. The extensions 64 in the rod pin 60 ride along the slots 90 in the shell 20 and the teeth 65 contact the cartridge teeth 85 and move above the level of the shell teeth 24. This movement causes the cartridge teeth 85 to disengage from the shell teeth 24 and engage with the rod pin teeth 65.

The axial movement of the rod pin 60 is translated to rotational movement of the cartridge 80 by the contact of the ramped teeth 65, 85. The ramped rod pin teeth 65 contact the ramped cartridge teeth 85. As the rod pin 60 moves axially, the cartridge teeth 85 slide along the rod pin teeth 65 thus causing rotation of the cartridge 80. The amount of rotation is controlled by the length of the ramped teeth because further rotation is prevented once the teeth 65, 85 become aligned. At some point, the shaft 50 is axially moved with the head 54 being above the cut-out 35.

The rotation of the cartridge 80 causes one of the chambers 84 that contains a fastener to align with the chute cut-out 35. Due to gravity, the fastener falls from the chamber 84 into the cut-out 35. When the shaft 50 is raised, the fastener continues falling via gravity through the opening 34 and into the interior of the shell 20. As the one chamber 84 moves over the cut-out 35, the other chambers 84 remain over the chute contact surface 33. The contact surface 33 supports the fasteners and prevents their inadvertent removal from their respective chambers 84.

After the fastener is in the shell 20, the shaft 50 is released moved axially in a downward direction. The biasing force of the spring 70 causes the rod pin 60 to remain in contact with and move downward with the head 54. At some point of downward movement, the shaft head 54 contacts the fastener and head of the fastener is positioned within the receptacle 53. Once positioned, either the shaft 50 or the entire tool 10 may be rotated to expel the fastener from the shell 20 and into the patient.

In one embodiment, as the shaft 50 is moved axially downward, the cartridge teeth 85 again come into contact with the shell teeth 24. This may be caused as the rod pin 60 slides downward along the shell 20. The contact between the teeth 85, 24 causes the cartridge 80 to partially rotate and become set for the next upward movement. In one embodiment, the shell teeth 24 are offset from the rod pin teeth 65 thus the cartridge rotates a first amount during upward movement of the shaft 50 and a second amount during downward movement of the shaft 50. In one embodiment, the teeth 24, 65, 85 are each substantially equal in shape and size. Therefore, upward axial movement of the shaft 50 and rod pin 60 causes a first amount of cartridge rotation as the teeth 65, 85 contact, and downward axial movement causes a second amount of rotation during contact with teeth 24, 85. When the teeth 24 are perfectly offset from teeth 65, the first and second amounts of movement are substantially the same. Different amounts of offset may cause the movement amounts to be different.

Offset of the teeth 24, 85 results in the contact of one set of teeth with a middle section of the ramped surface of the opposing teeth. This allows for rotation of the cartridge 80. In the event the teeth were not offset (i.e., the teeth were aligned), there would be no radial movement as the steps of the teeth would be aligned and provide for no sliding movement.

Subsequent fasteners may be released from the cartridge 80 and enter into the shell 20 by repeating the upward movement of the shaft 50.

Figure 12:
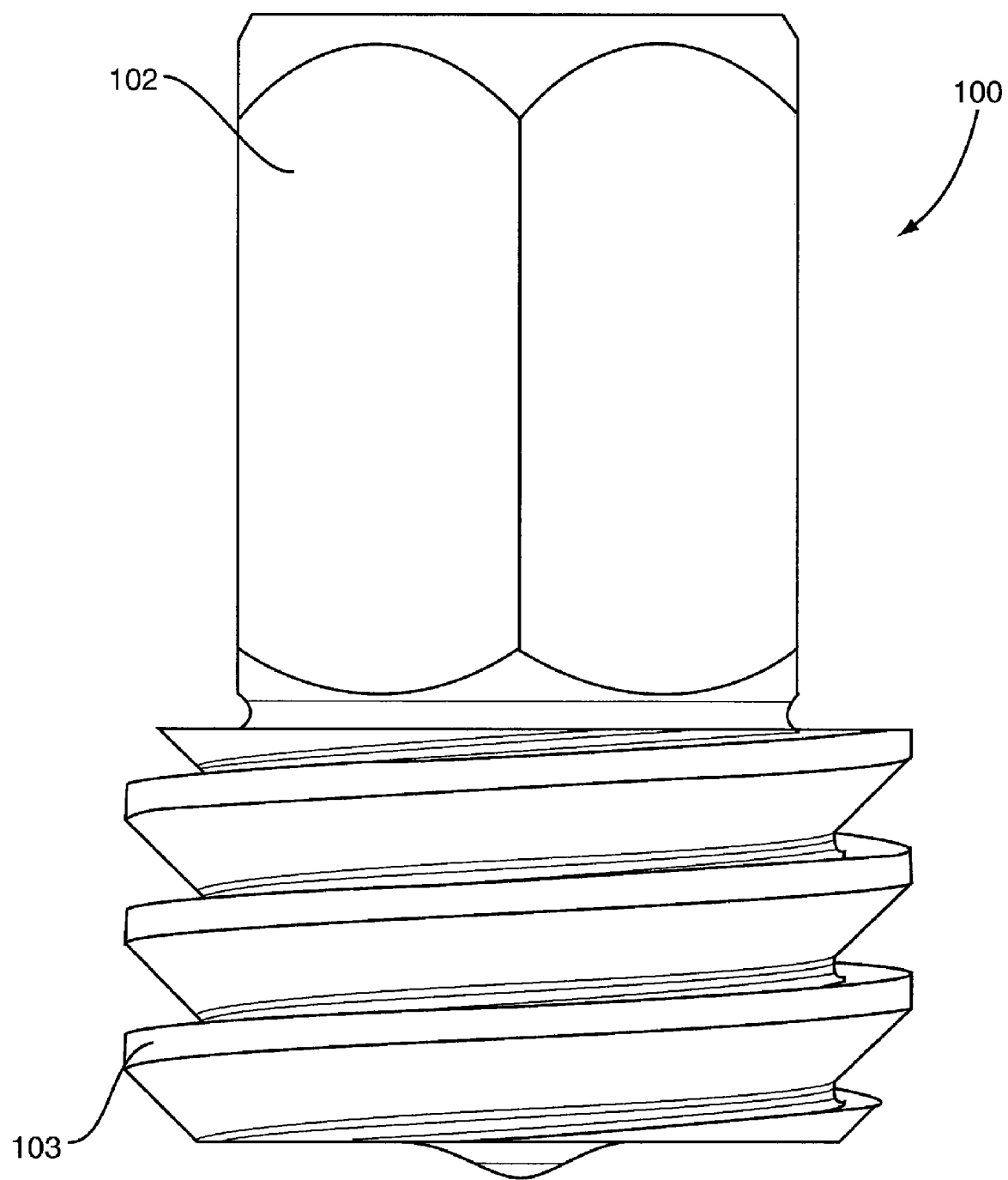
FIG. 12 is a side view of a fastener used with one embodiment of the tool.

Various types of fasteners may be used with the tools 10. FIG. 12 illustrates one type of fastener 100 with a head 102 and a mounting section 103. The head 102 is sized to be mounted within the receptacle 53 at the second end of the shaft 50. One use for this type of fastener is to contain a vertebral rod within a channel. Another type of fastener is CD Horizon Legacy Higher Clamp Break-Off Set Screws, available as part number 7560020 from Medtronic Sofamor Danek of Memphis, Tenn.

In the embodiment of FIG. 2, two separate springs 70, 71 are used to bias the elements. In other embodiments, the tool 10 includes a single spring or three or more springs. Still other embodiments include no springs.

In some embodiments described above, the fasteners fall via gravity from the chambers 84 into the chute 30. In another embodiment, the chambers 84 may include a spring to bias the fasteners upward (i.e., against gravity). The fasteners may be biased individually from the chambers 84 when the cartridge 80 is indexed.

Figure 13:
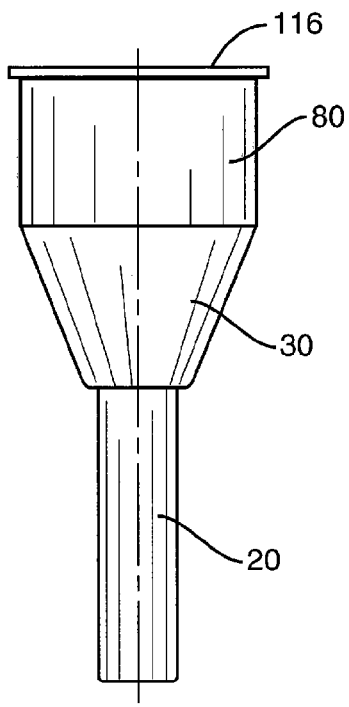
FIG. 13 is a side view of a tool for holding one or more fasteners according to one embodiment.

In embodiments described above, rotation of the cartridge 80 is caused by axial movement of the shaft 50. In another embodiment as illustrated in FIG. 13, the surgeon manually rotates the cartridge 80. At least a section of the cartridge 80 is exposed to allow the surgeon to manipulate and rotate the cartridge 80. As described above, the rotation causes each chamber 84 to individually move past a section of the chute 30 and be expelled from the cartridge 80. A lid 116 may extend across an upper surface of the cartridge 80 to prevent the fasteners from escaping.

In one embodiment, the chambers 84 are constructed to hold multiple fasteners. When the cartridge 80 is rotated over the chute 30, a single fastener may be expelled from the chamber 84. Alternatively, two or more fasteners within the chamber 84 may be expelled.

Figure 14:
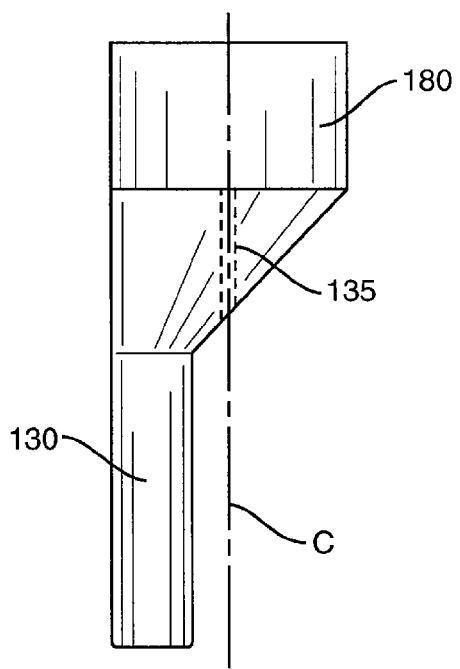
FIG. 14 is a side view of a tool for holding one or more fasteners according to one embodiment.

FIG. 14 illustrates another embodiment with a stationary cartridge 180. Cartridge 180 includes one or more chambers as discussed in the embodiments above. A chute 130 is movably connected to the cartridge 180. A connector 135 may extend from a center of the cartridge 180 and attach to the chute 130. Connector 135 provides for rotating the chute 130 about the lower end of the cartridge 180. In use, the surgeon may hold the cartridge 180 with a first hand, and the chute 130 with a second hand. Chute 130 is rotated to a first chamber causing a fastener in the chamber to move into the chute 130.

Chute 130 may then be rotated to another chamber to dispense another fastener. In one embodiment, the cartridge 180 and chute 130 may each include roughened or knurled surfaces to facilitate grasping by the surgeon.

In some embodiments as illustrated in FIG. 2, fasteners are moved in a radial direction towards a centerline C of the tool 10. In these embodiments, the chambers 84 are arranged around the periphery of the cartridge 80. The chute 30 is then constructed to radially move the fasteners towards the centerline C. In other embodiments as illustrated in FIG. 14, the fasteners remain spaced from the centerline C. The fasteners are housed in chambers around the periphery of the cartridge 180 and remain spaced away from the centerline C when moved into the chute 130.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A surgical tool for inserting fasteners during a surgical procedure, the tool comprising:
   a cartridge including a plurality of chambers each sized to hold at least one of the fasteners;
   a receiving element positioned axially below the cartridge, the receiving element including a first end and a second end, the first end including a contact surface aligned with the chambers and positioned to contact the fasteners and prevent the fasteners from exiting the chambers, the receiving element further including a chute that includes an opening at the contact surface and extends to the second end;
   an engagement member positioned axially below the cartridge and being movable axially within an interior of the receiving element;
   a shaft that extends through the cartridge, the engagement member, and the receiving element;
   the shaft being axially movable relative to the cartridge to move the engagement member into contact with the cartridge to rotate the cartridge to individually index the chambers into alignment with the opening of the chute thereby causing the fastener held in the aligned chamber to be released from the aligned chamber and moved along the chute.

2. The tool of claim 1, wherein the cartridge further includes a central opening positioned radially inward from each of the plurality of chambers.

3. The tool of claim 1, wherein each of the plurality of chambers includes a first section with a first cross-sectional shape and a second section with a different second cross-section shape.

4. The tool of claim 1, wherein the chute angles radially inward from the first end to the second end.

5. The tool of claim 1, further comprising a plurality of teeth each with a ramped configuration and being operatively connected to the shaft, the axial movement of the shaft causing the plurality of teeth to engage the cartridge and causing the cartridge to rotate.

6. The tool of claim 1, further comprising a lid that extends over a section of the cartridge.

7. The tool of claim 1, further comprising an elongated shell that is positioned at the second end of the receiving element, the shell including a hollow interior sized to receive the fasteners and position the fasteners.

8. A surgical tool for inserting fasteners during a surgical procedure, the tool comprising:
   a cartridge including a first central opening and a plurality of chambers positioned radially outward from the first central opening, each of the plurality of chambers sized to hold one or more of the fasteners;
   a funneling element positioned axially adjacent to the cartridge and including a first end that faces towards the cartridge and a second end that faces away from the cartridge, the funneling element further including a second central opening that extends from the first end to the second end and is aligned with the first central opening of the cartridge, the funneling element further including a chute that angles radially inward from the first end to the second end;
   an engagement member with a third central opening, the engagement member positioned to extend into the second central opening and contact against the cartridge;
   a shaft with an elongated shape that extends through the first, second, and third central openings, the shaft being movable within the first and second central openings to contact the engagement member against the cartridge;
   the chute individually aligning with the chambers to receive the fastener of the aligned chamber and guide the fastener radially inward as the fastener moves from the first end to the second end of the funneling element.

9. The tool of claim 8, further comprising a biasing mechanism that biases the cartridge towards the funneling element.

10. The tool of claim 8, wherein the funneling element further includes a contact surface adjacent to the chute that aligns with the chambers to contact the fasteners and prevent the fasteners from exiting the chambers.

11. The tool of claim 8, wherein the cartridge further includes teeth that are engaged during axial movement of the shaft causing rotation of the cartridge.

12. The tool of claim 8, wherein the shaft includes opposing ends, the shaft movable between a first orientation with the funneling element positioned between the opposing ends and a second orientation with the funneling element positioned outside of the opposing ends.

13. The tool of claim 8, further comprising an elongated guide extending from the second end of the funneling element, the guide including a hollow interior sized to receive the fasteners after being moved from the chamber and through the chute.

14. A surgical tool for inserting fasteners during a surgical procedure, the tool comprising:
   a top member;
   a cartridge including a first central opening and a plurality of chambers positioned radially outward from the first central opening, each of the plurality of chambers sized to hold one or more of the fasteners;

a receiving element positioned axially adjacent to the cartridge and including a first end that faces towards the cartridge and a second end that faces away from the cartridge, the receiving element further including a second central opening that extends from the first end to the second end and is aligned with the first central opening of the cartridge, the receiving element further including a chute;

an elongated shaft axially movable within the first and second central openings, the shaft movable in a first axial direction to rotate the cartridge thereby moving one of the plurality of chambers into alignment with the chute and causing the fastener held in the aligned chamber to release from the aligned chamber and move along the chute; and a hollow rod pin that extends around the shaft and is positioned on an opposite side of the cartridge from the top member, the rod pin including teeth that engage the cartridge during movement of the shaft in the first axial direction thereby causing rotation of the cartridge.

15. The tool of claim 14, wherein the chute includes an angled surface that directs the fasteners from each of the chambers radially inward towards a tool centerline.

16. The tool of claim 14, wherein the receiving element further includes a contact surface adjacent to the chute that aligns with the chambers to contact the fasteners and prevent the fasteners from exiting the chambers.

17. A surgical tool for inserting fasteners during a surgical procedure, the tool comprising:

a cartridge including a first central opening and a plurality of chambers positioned radially outward from the first central opening, each of the plurality of chambers sized to hold one of the fasteners;

a receiving element positioned axially adjacent to the cartridge and including a second central opening that extends through the receiving element and is aligned with the first central opening of the cartridge, the receiving element further including a chute;

an elongated shaft axially movable within the first and second central openings; and a rod pin sized to extend around the shaft and fit within the second central opening;

the shaft movable in a first axial direction to move the rod pin into contact with the cartridge and rotate the cartridge thereby moving one of the plurality of chambers into alignment with the chute and causing the fastener held in the aligned chamber to release from the aligned chamber and move along the chute.

* * * * *